(12) United States Patent
Baker et al.

(10) Patent No.: US 7,787,642 B2
(45) Date of Patent: Aug. 31, 2010

(54) LOW-POWER HIGH-PSRR CURRENT-MODE MICROPHONE PRE-AMPLIFIER SYSTEM AND METHOD

(75) Inventors: Michael W. Baker, Cambridge, MA (US); Micah O'Halloran, Hyde Park, MA (US); Rahul Sarpeshkar, Arlington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1194 days.

(21) Appl. No.: 10/892,932

(22) Filed: Jul. 16, 2004

(65) Prior Publication Data
US 2008/0002841 A1    Jan. 3, 2008

Related U.S. Application Data

(60) Provisional application No. 60/488,148, filed on Jul. 17, 2003.

(51) Int. Cl.
*H04R 3/00* (2006.01)
(52) U.S. Cl. .................. 381/113; 381/111; 381/122; 330/260; 330/308
(58) Field of Classification Search ......... 381/111–115, 381/61, 26, 91–92, 120, 122; 330/257, 260, 330/69, 105, 288, 290, 308, 98
See application file for complete search history.

(56) References Cited

U.S. PATENT DOCUMENTS

| | | | |
|---|---|---|---|
| 5,083,095 A | 1/1992 | Madaffari | |
| 5,239,579 A * | 8/1993 | Schuh | 379/395 |
| 5,337,011 A | 8/1994 | French et al. | |
| 5,459,792 A * | 10/1995 | Reichel et al. | 381/111 |
| 5,627,494 A * | 5/1997 | Somerville | 330/257 |
| 5,717,773 A * | 2/1998 | Maag et al. | 381/98 |
| 6,104,818 A * | 8/2000 | Korner | 381/113 |
| 6,118,991 A * | 9/2000 | Jean et al. | 455/293 |
| 6,151,967 A * | 11/2000 | McIntosh et al. | 73/514.32 |
| 6,160,450 A | 12/2000 | Eschauzier et al. | |
| 6,204,728 B1 * | 3/2001 | Hageraats | 330/98 |
| 6,492,796 B1 | 12/2002 | Morley | |
| 6,516,069 B1 * | 2/2003 | Takeuchi et al. | 381/122 |
| 6,608,905 B1 * | 8/2003 | Muza et al. | 381/111 |

* cited by examiner

*Primary Examiner*—Xu Mei
*Assistant Examiner*—Disler Paul
(74) *Attorney, Agent, or Firm*—Gauthier & Connors LLP

(57) ABSTRACT

A low power high dynamic range microphone amplification system is disclosed. The system includes a current sensing amplifier for receiving an input current signal representative of auditory information and for providing an amplifier output signal. The current sensing amplifier includes a DC bias network that includes a cascode filter.

19 Claims, 15 Drawing Sheets

LOW-POWER HIGH-PSRR CURRENT-MODE MICROPHONE PRE-AMPLIFIER SYSTEM AND METHOD

PRIORITY

This application claims priority to U.S. Provisional Application Ser. No. 60/488,148 filed Jul. 17, 2003.

BACKGROUND OF THE INVENTION

The invention generally relates to hearing aids and particularly relates to cochlear implants. Hearing impairment is believed to affect approximately 10% of individuals in the world. Many such individuals are in need of cochlear implants or hearing aids to listen to normal sounds. Conventional hearing instruments are designed to fit inside the ear, requiring small, low power, wide-dynamic-range front ends with a minimum of external components and good power supply rejection.

The use of wideband clock and telemetry signals in hearing instruments further requires a very high level of superb power-supply rejection in-band as well as at high frequencies. A fully analog hearing instrument should exhibit good power-supply rejection properties in all of its stages prior to rectification. A digital signal processor (DSP)-based hearing instrument should also have good power supply rejection in the analog front-end to ensure that the analog-to-digital (A/D) system is not exposed to aliasing and distortion errors caused by high-frequency supply noise.

Further, wide dynamic range is needed to meet patient needs in noisy environments. Hearing instruments are typically limited to 83 dB of input dynamic range by available microphone technology. Peak signals therefore, of 110 dBSPL and a microphone noise-floor of 27 dBSPL, make most hearing tasks possible. Typical low power microphones such as JFET buffered microphones with an electret capacitor provide an output voltage signal with good dynamic range, but that may fluctuate slightly with fluctuations in the power supply. Such fluctuations, or noise, may significantly detract from the microphone and pre-amplifier performance.

There is a need therefore, for improved low power wide-dynamic range microphone systems for hearing aids and cochlear implants. There is further a need for low power microphone systems that provide improved power supply noise rejection.

SUMMARY

The invention provides a low power high dynamic range microphone amplification system. In accordance with an embodiment, the system includes a current sensing amplifier for receiving an input current signal representative of auditory information and for providing an amplifier output signal. The current sensing amplifier includes a DC bias network that includes a cascode filter.

In further embodiments, the invention provides a low power high dynamic range microphone amplification system. The system includes a self-biased microphone circuit, a current sensing amplifier, and a feedback network. The self-biased microphone circuit provides a current signal that is representative of auditory information. The current sensing amplifier receives the current signal at an amplifier input node and provides an amplifier output signal at an amplifier output node. The feedback network includes a high frequency feedback path and a low frequency feedback path.

In accordance with another embodiment, the invention provides a transistor current source including a first transistor with a supply voltage node, a control signal node and an output current node, and a second transistor including a current receiving node for receiving current from the first transistor, a control node and an output node, wherein the output node of the first transistor is coupled to the current receiving node of the second transistor and is coupled to a first filter element.

BRIEF DESCRIPTION OF THE DRAWING

The following description may be further understood with reference to the accompanying drawings in which.

The drawings are shown for illustrative purposes and are not to scale.

DETAILED DESCRIPTION OF THE ILLUSTRATED EMBODIMENTS

The invention provides a low voltage microphone system in which a JFET microphone buffer's output current, rather than its output voltage, is transduced via a sense-amplifier topology allowing good in-band power-supply rejection in accordance with an embodiment. The design employs a low-frequency feedback loop to subtract the D.C. bias current of the microphone and prevent it from causing saturation. Wideband power-supply rejection is achieved by integrating a filter on all current-source biasing. In an embodiment, the design exhibits 80 dB of dynamic range with less than 5 µVrms of input noise while operating from a 2.8V supply. The power consumption is 96 µW which includes 60 uW for the microphone built-in buffer. The in-band power-supply rejection ratio (PSRR) varies from 50 dB to 90 dB while out-of-band supply attenuation is greater than 60 dB until 25 MHz. Fabrication may be achieved in a 1.5 µm CMOS process with gain programmability for both microphone and auxiliary channel inputs.

Figure 1:
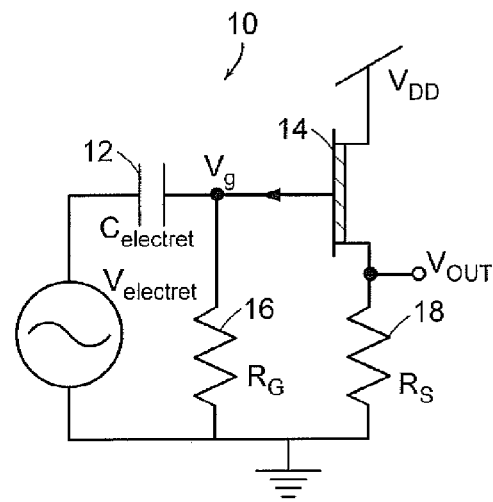
FIG. 1 shows an illustrative diagrammatic schematic view of a sub-miniature microphone circuit for use in a system in accordance with an embodiment of the invention.

As shown in FIG. 1, a sub-miniature microphone for hearing aids and cochlear implants that is suitable for use in an embodiment of the invention may be a self-biased MOS device that buffers the voltage from a moving electret capacitor. In particular, the microphone circuit 10 may include an electret capacitor 12 ($C_{electret}$) that produces a voltage responsive to sound (shown as a voltage source $V_{electret}$) a low-noise depletion-mode MOSFET device 14, a gate resistor 16 ($R_G$) and a source resistor 18 ($R_S$). The output from the buffer is taken at the source of the MOS device, providing a relatively low-impedance voltage output ($V_{OUT}$).

Such a self-biased structure is typically employed to obtain insensitivity to the drain supply voltage, $V_{DD}$. The presence of finite output resistance, however, can make the effect of supply noise on the output signal quite pronounced. This problem may be quite serious in certain applications as many high-frequency signals are present in the implant/hearing-aid environment including carriers for power transfer and communications. Because the output voltage $V_{OUT}$ is provided in series between the source resistor 18 and the MOSFET device 14, any fluctuations in $V_{DD}$ at high frequencies may directly transfer to $V_{OUT}$. Feed-through of high-frequency carriers is problematic when non-linear elements rectify this content to in-band signal frequencies. A small signal model of the self-biased buffer structure may be employed to analyze the system wherein the output resistance of the MOS device is represented as $r_o$ and the device's transconductance is represented as $g_m$. The model also includes active device and parasitic gate and source resistances and capacitances represented as $r_o$, $R_s C_{GD}$ and $C_{GS}$.

The contributing mechanisms for power-supply feed-through may be represented, therefore, as a summing of currents of relating to $$g_0 + \frac{sC_{GD}C_{GS}}{C_T} + \frac{g_m C_{GD}}{C_T} - \frac{g_m C_{GS}}{C_T}$$

(from a feedback path), which provides $$\frac{1}{sC_{GS} + g_m + g_0}.$$

The output conductance $g_o$ and gate capacitances contribute to power-supply tones at $v_{out}$. Since the gain of the buffer stage to the transduced electret voltage approaches unity, the power supply rejection ratio (PSRR) of this topology is simply the inverse of the feed-through function. Assuming $v_{out}$ is grounded, the short-circuit current measured at $v_{out}$ is due to feed-through from drain-to-source conductance, $g_0$, direct capacitive feedthrough, and capacitive-divider and JFET transconductance interaction. These terms determine $i_{sc}$. The output impedance measured at $v_{out}$ with $v_{dd}$ and $v_{in}$ grounded is given by the feedforward block, $$\frac{1}{sC_{GS} + g_m + g_o}$$

if the $g_m v_g$ term of the dependent source is ignored. Including the $g_m v_g$ term of the dependent source adds a feedback block from the output with gain $$\frac{sC_{GS}}{C_T}.$$

Combining these effects, assuming that $C_{Electret} \gg C_{GD}$, $C_{GS}$, and using Black's formula for feedback loops provides, $$\frac{v_{out}}{v_{dd}} = \frac{\left(\frac{C_{GD}}{C_T}\right)(sC_{GS} + g_m + g_o)}{sC_{GS} + g_m + g_o + g_m\left(\frac{C_{GS}}{C_T}\right)} \cong \frac{\left(\frac{C_{GD}}{C_T}\right)(sC_{GS} + g_m)}{sC_{GS} + g_m + g_m\left(\frac{C_{GS}}{C_T}\right)} \quad (1)$$

where, $C_T = C_{GS} + C_{GD} + C_{Electret}$. In many cases, a large FET structure, used to get low-noise operation, results in a large gate-to-drain capacitance. As Equation (1) shows, the large gate-to-drain capacitance results in capacitive feed-through of the supply to the output, directly and via the $g_m$ generator. The challenge of designing high-PSRR front-ends without redesigning the internal structure of modem sub-miniature microphones requires thorough design efforts. While some microphone designs do away with the FET buffer, such a design choice requires manufacturing modifications that are not available to low-cost producers.

A suitable microphone for use in certain embodiments of the invention may be a Knowles FG-3329A sold by Knowles Acoustics division of Knowles Electronics Holdings, Inc. of Itasca, Ill., which has an operating drain voltage range of 0.9 V-1.6 V and draws 15 µA-30 µA from the supply. The source resistance, $R_S$, may be measured to be 20 kΩ. Internal gate-to-source and gate-to-drain capacitances may be approximately, 80 pF and 120 pF, respectively, while the electret capacitance may be estimated to be 1 nF. The measured power supply rejection was 22 dB. The total noise from 100 Hz to 10 kHz was found to be less than 4 μVrms at the output node, $V_{OUT}$.

Figure 2:
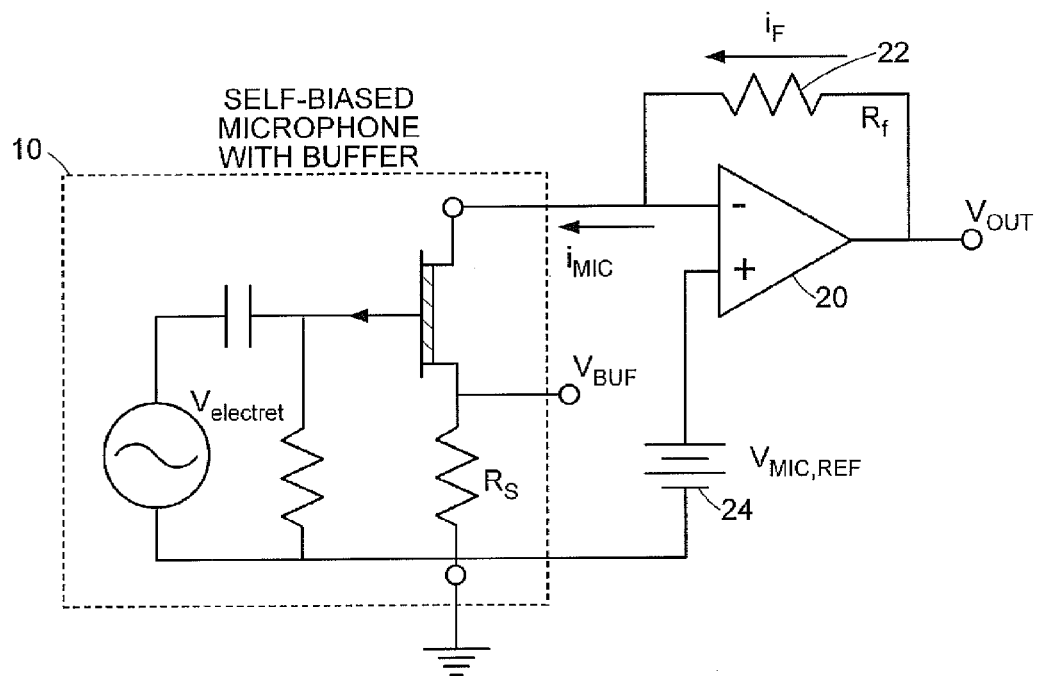
FIG. 2 shows an illustrative schematic view of a system in accordance with an embodiment of the invention that employs the sub-miniature microphone circuit of FIG. 1.

In accordance with an embodiment, the invention provides a self-biased microphone structure that may be configured as the input to a sense amplifier allowing voltage regulation of the drain node as shown in FIG. 2. The system includes the microphone circuit 10 from FIG. 1, an amplifier 20, an amplifier feedback resistor 22 coupling the output of the amplifier to a negative input of the amplifier, and a microphone reference voltage ($V_{MIC,REF}$) 24 coupled to a positive input of the amplifier 20. The voltage source for the microphone circuit 10 is coupled to the negative input to the amplifier 20. During operation, the current from the microphone is in effect sensed, rather than its voltage being provided at a voltage output node. The sensed current is then converted to an output voltage through $R_F$. The larger the value of $R_F$, the larger is the sensitivity of the microphone to sound. The output impedance of the amplifier 20 is low, due to the feedback of the circuit.

Fluctuations in supply voltage, therefore, are buffered through the amplifier 20. Biasing current for the microphone flows through the feed-back load, $R_F$, such that, $v_{OUT} = V_{MIC,REF} + i_F R_f$. Referring this new output to the normal output of the buffer, $v_{buf}$, provides, $$\frac{v_{out}}{v_{buf}} = \frac{i_{MIC} R_f}{i_{MIC} R_S} = \frac{R_f}{R_S} \qquad (2)$$

Figure 3A:
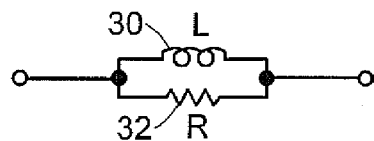
FIGS. 3A and 3B shows illustrative diagrammatic schematic views of frequency dependent feedback networks for use in systems in accordance with various embodiments of the invention.
Figure 3B:
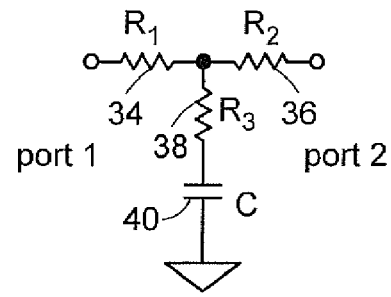

The front-end gain or sensitivity may, therefore, be programmed by selecting the feedback impedance, $R_f$. More generally, the feedback resistor may be replaced by a two-port network, $Y_f$, whose current at the input side and at the output side is a linear function of the voltages at the input and output sides. Since the microphone buffer current is comprised of a large DC component, $I_{MIC}$, the output linear range of the operational amplifier in the sense-amp is degraded by the voltage drop, $I_{MIC} R_f$. To make high gain possible while preserving linear range, various two-port networks may be used in place of $R_f$. Two examples of such two-port networks are shown in FIGS. 3A and 3B. As shown in FIG. 3A, one network includes an inductor 30 in parallel with a resistor 32, and as shown in FIG. 3B, another such network includes a pair of series resistors 34, 36 with a third resistor 38 in series with a capacitor 40 extending from the junction of the resistors 34 and 36, and ground. These each provide frequency dependent feedback networks that may mitigate the effects of DC current in the feedback path, and each has good AC gain and also permits the bias current, $I_{MIC}$, to be sourced without taking the op-amp out of its linear DC output operating range.

The network of FIG. 3A shows a choice for a two-port network that does not sacrifice any output linear range while maintaining a suitable AC sense-gain of R. On-chip solutions, however, obviate the use of inductors. On-chip solutions may apply the T-network solution of FIG. 3B. In the T-network of FIG. 3B, $$V_{DC} = I_{MIC}(R_1 + R_2) \qquad (3)$$

The high-frequency cross-conductance to obtain gain at $v_{out}$ is calculated by shorting C, shorting the input port FIG. 3B, and measuring the short-circuit current at the port as a function of $v_{out}$. It is found to be given by, $$y_2 = \frac{R_3}{R_1 R_2 + R_1 R_3 + R_2 R_3}. \qquad (4)$$

Figure 4:
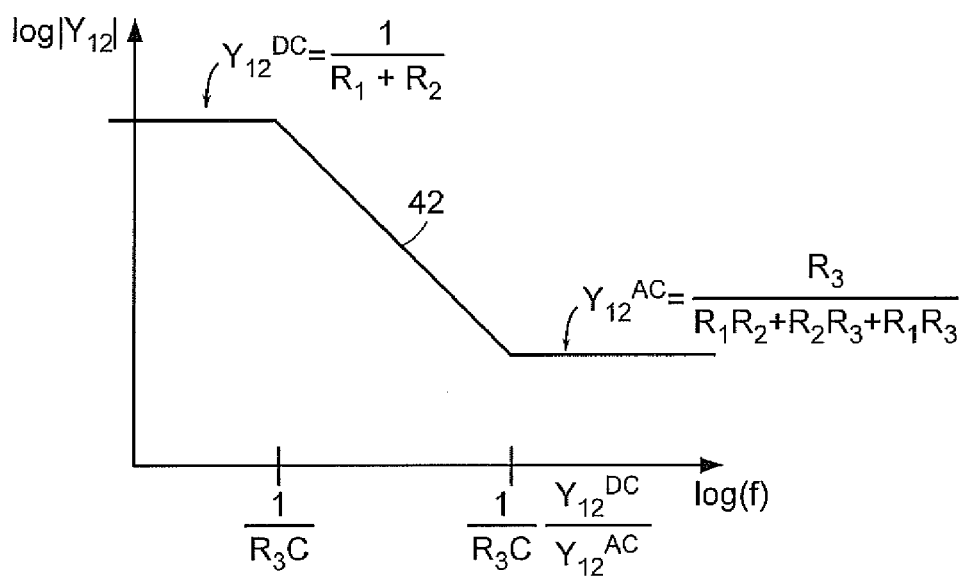
FIG. 4 shows an illustrative diagrammatic graphical view the frequency dependent conductance of a system in accordance with an embodiment of the invention.

The T-network network in effect forms a current divider at high-frequencies and attenuates current in the feedback path. Thus, it provides gain at high-frequencies. At low-frequencies, there is no current attenuation, so the DC gain is lower. FIG. 4 shows the frequency-dependent conductance 42 of the T-network shown in FIG. 3B.

A small DC voltage drop from $v_{OUT}$ to the sense-node at $V_{MIC,REF}$ is achieved when the total series resistance, $R_1 + R_2$, is sufficiently small. Making $R_3 C$ large yields better gain (larger $1/y_{12}$) at low frequencies as shown in FIG. 4. To obtain a high ratio between $Y_{12}^{DC}$ and $Y_{12}^{AC}$, $R_3$ is chosen to be much smaller than $R_1$ or $R_2$. At high frequencies, the capacitor 40 in the shunt branch of the T-network shown in FIG. 3B is an AC short-circuit. As a result, the driving-point impedance at port 1, $1/y_{11}$, is $R_1 + R_3$ while the driving-point impedance at port 2, $1/y_{22}$, is $R_2 + R_3$. Since $R_3$ is small, this may be approximated to be zero when computing the driving-point impedances at either port. The T-network, therefore, of FIG. 3B permits DC current to flow through the feedback element, $Y_f$. The DC current may therefore be used as part of the output stage biasing of the op-amp.

Figure 5:
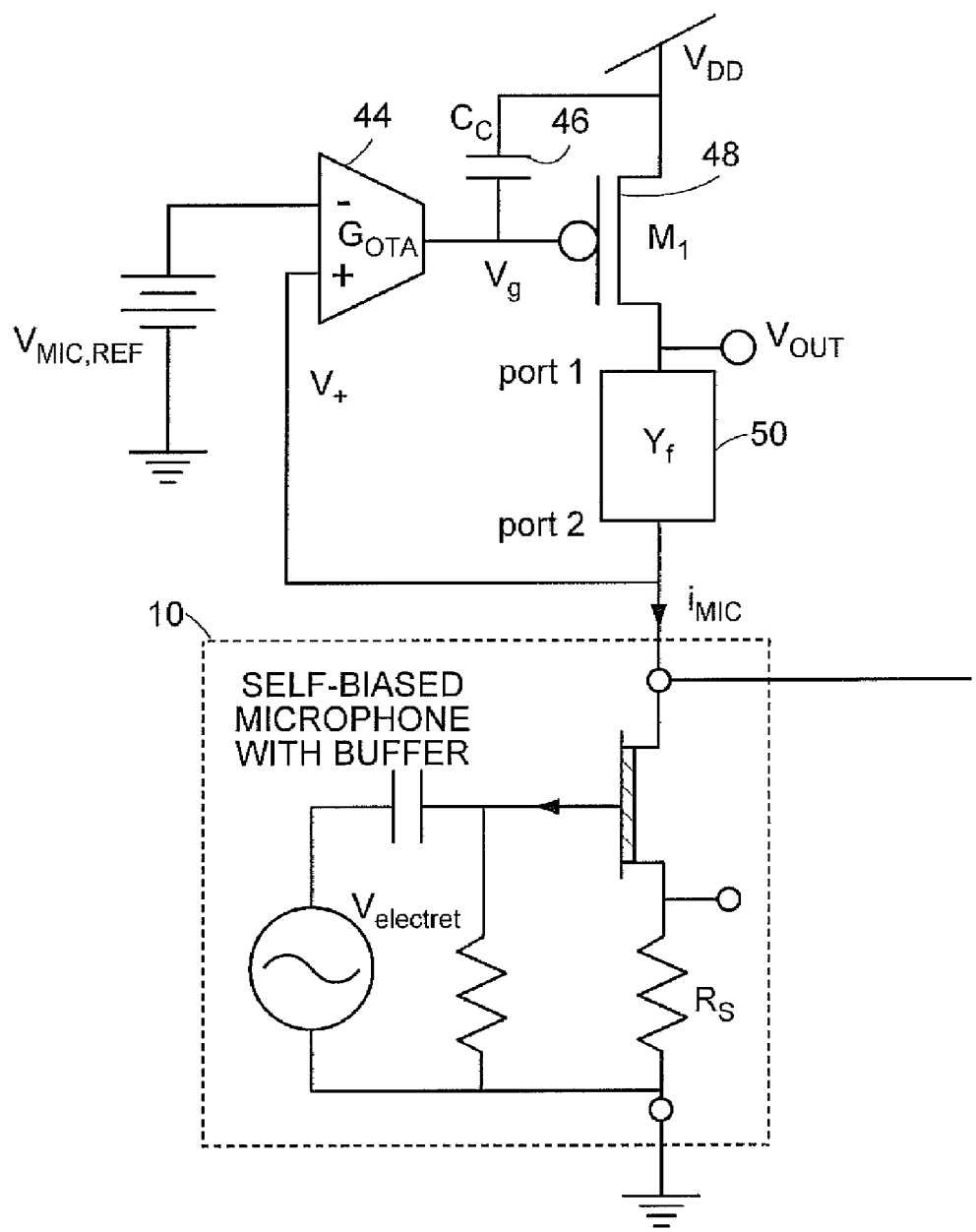
FIG. 5 shows an illustrative diagrammatic schematic view of a system in accordance with another embodiment of the invention that employs the sub-miniature microphone circuit of FIG. 1.

As shown in FIG. 5, a single device may be employed as the output stage of the amplifier, providing both DC current and pre-emphasis for a microphone circuit 10, with a feedback loop as discussed above to preserve negative feedback. In FIG. 5, the amplifier is shown schematically as having two components, the transconductor 44 and the output device 48. These together are one possible implementation of the amplifier 20 shown in FIG. 2. The ports on the feedback element are labeled for clarity. In addition to the self-biased microphone with buffer 10, the system includes an amplifier 44 with gain $G_{OTA}$, a capacitor 46 ($C_C$) coupling the source and gate of an FET 48 ($M_1$), and a frequency dependent feedback network 50 ($Y_f$) as discussed above with reference to FIGS. 3A and 3B.

Some limitations of the approach shown in FIG. 5 become apparent when the requirements on the feedback T network are reviewed. First, the distortion at the output node, $v_{OUT}$, is dominated by the signal swing range on the gate and drain of $M_1$. The gain of the $M_1$ amplifier stage is set by $g_{M1}/y_{12}$, or simply, $g_{M1}(R_1 + R_3)$. If the gain of the $M_1$ stage is too low, then the swing at the gate, for a given maximum desired output voltage swing, is larger than the overdrive voltage of $M_1$, ($V_{GS,1} - V_{T1}$), causing distortion. Therefore $R_1 + R_3$ must be large. At the drain of the microphone, the driving point impedance is $y_{21}$, or $R_2 + R_3$. The current noise contributed to the sense-node from these discrete resistors is, $$\frac{4kT}{R_2 + R_3}.$$

Figure 6:
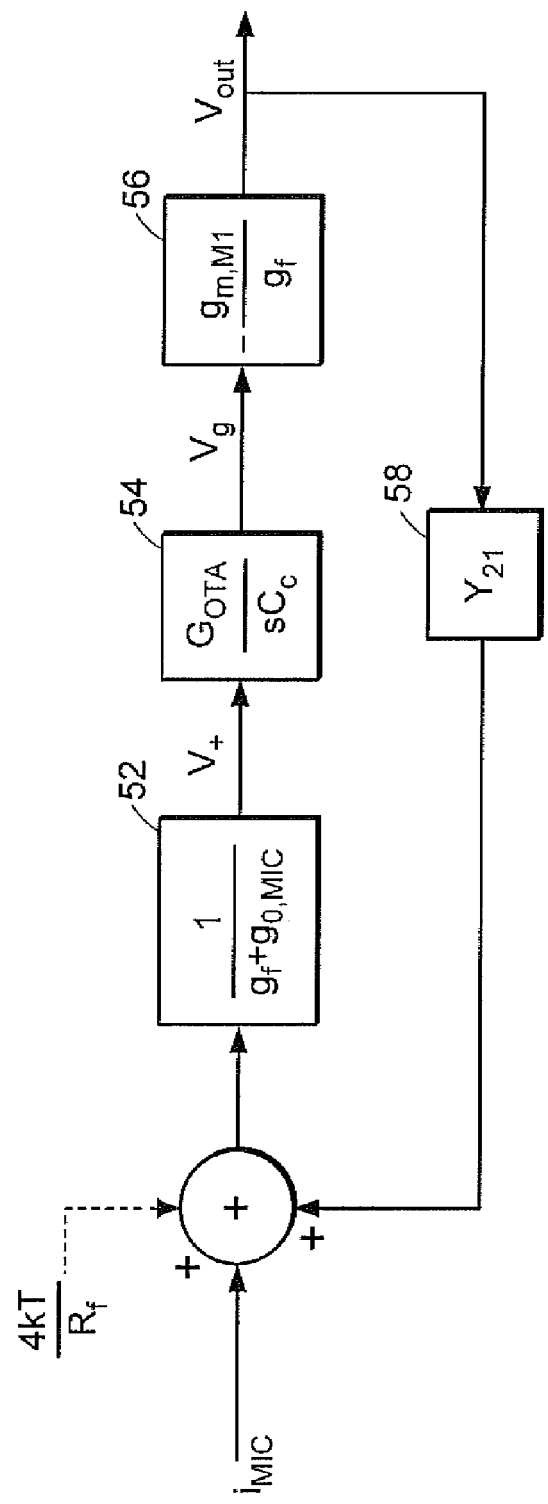
FIG. 6 shows an illustrative diagrammatic schematic view of a sense-amp topology for a system in accordance with an embodiment of the invention.

This noise source is included in FIG. 6, where for notational simplicity, $R_f$ is used to represent $R_2 + R_3$. As shown, the feedback path of the small-signal block diagram for the sense-amp topology for the circuit of FIG. 5 includes the forward elements 52, 54 and 56, as well as the feedback element 58. Noise contributed to the sense node by the feedback network is also shown. To ensure low-noise operation $R_2 + R_3$ must be large. Consequently both $R_1$ and $R_2$ must be large, making it difficult to satisfy a small voltage drop across the T-network by Equation (3). The dynamic range of this topology is limited due to the conflicting constraints on $R_1$ and $R_2$. The flow of DC current through the feedback network causes limitations to the dynamic range through both noise and distortion effects. Thus it is advantageous to have no DC current through the feedback network.

Figure 7:
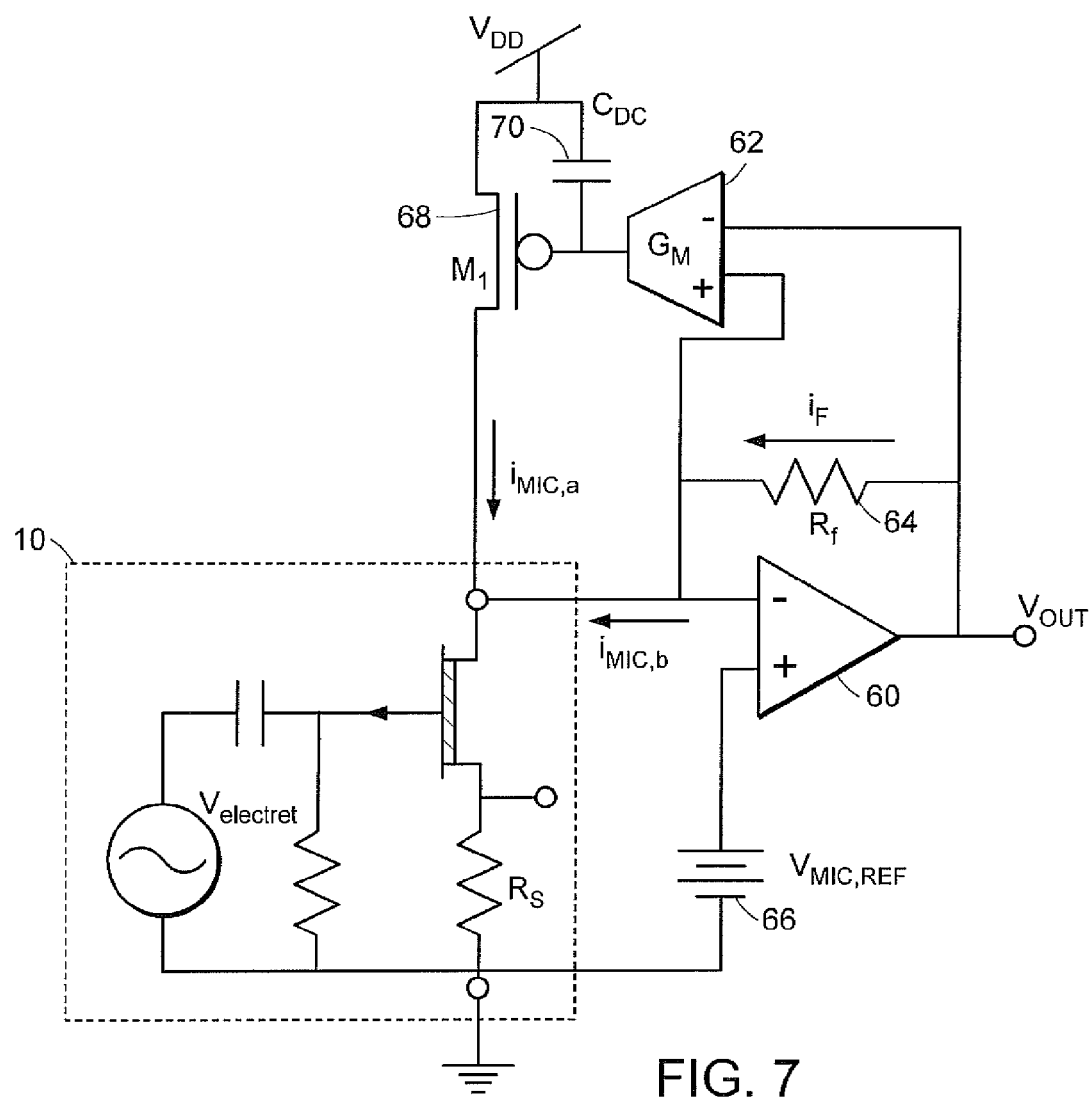
FIG. 7 shows an illustrative diagrammatic view of a system in accordance with a further embodiment of the invention that employs the sub-miniature microphone circuit of FIG. 1.

As shown in FIG. 7, a system in accordance with another embodiment of the invention provides a split-frequency feedback technique that prevents DC current from flowing through the feedback network. The circuit includes a first amplifier 60 as well as a second amplifier 62. The first amplifier 60 is coupled to the microphone circuit 10 similar to the coupling of the amplifier 20 to the circuit 10 of FIG. 2 using a feedback resistor 64 ($R_f$) and reference voltage 66 ($V_{MIC,REF}$). The positive input to the second amplifier 62 is provided by the negative input of the first amplifier 60 (as well as the voltage source input for the circuit 10), and the negative input of the second amplifier 62 is provided by the output of the first amplifier 60. The output of the second amplifier 62 is provided to a gate of an FET 68 as shown, and is coupled to $V_{DD}$ and the source of the FET 68 via a capacitor 70 ($C_{DC}$). The drain of the FET 68 is coupled to the voltage source input for the circuit 10.

Figure 8:
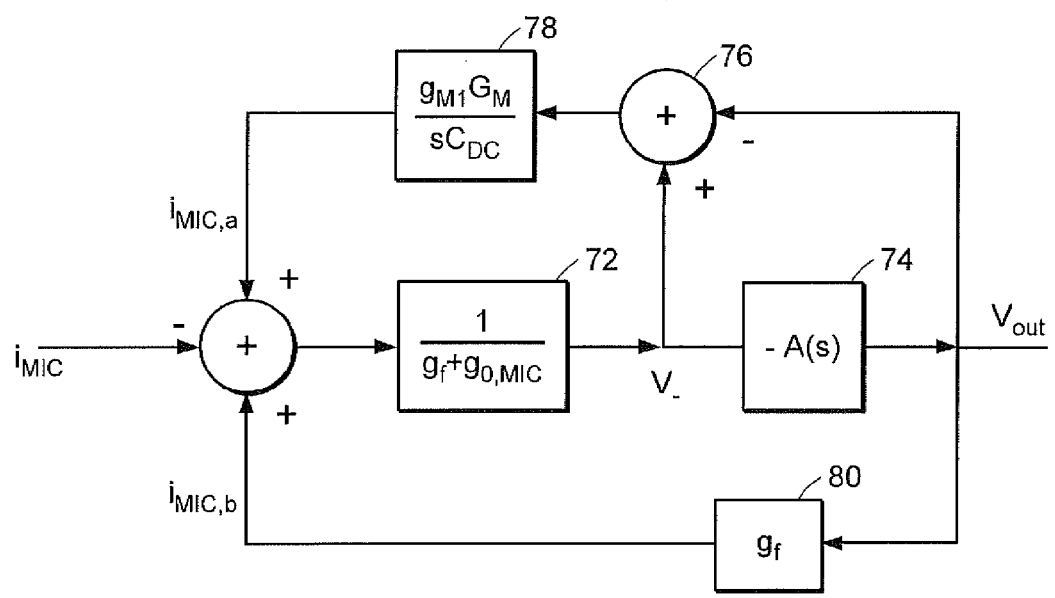
FIG. 8 shows an illustrative diagrammatic schematic view of the functional operation of the topology shown in FIG. 7.

The transconductor amplifier 62 acts to cancel any low-frequency and DC voltage drop in the feedback network. The amplifier 62 and the capacitor 70 ($C_{DC}$) form a low-pass filter which drives transistor 68 ($M_1$) to subtract low-frequency current from the sensing node. This slow loop then ensures that there is no sensing of the DC current from the microphone while the normal fast sense-amplifier loop transduces the AC current from the microphone into an output AC voltage. This approach retains the benefit of the current mode scheme. With reference to FIG. 7, by driving the DC drop across the sense-amp resistor to zero with feedback, the bias current of the microphone may be subtracted, preventing it from causing saturation effects in the operational amplifier. The cancellation of the DC output current may be imperfect without seriously degrading performance. A feedback block diagram for this system is shown in FIG. 8, indicating both low-frequency and high-frequency loops. In particular, a common forward path includes two elements 72 and 74, while a first feedback path includes a combiner 76 and another element 78, while a second feedback path includes an element 80. Because the low-frequency loop may be made arbitrarily slow, its dynamics may be designed so as to not interfere with the high-frequency loop stability. Stabilizing the overall system may then be done without considerations for the performance of the low-frequency biasing loop. Microphone response to unwanted low-frequency vibrations may be reduced through selection of the dynamics of the low-frequency loop.

This approach also provides flexibility in the choice of feedback elements. If frequency dependent feedback is to be used, it is no longer required to carry appreciable DC current. If high-pass filtering is desired, a T-network may be used. As no bias current flows through the T-network, the total series resistance in it, $R_1+R_2$, may now be large to ensure low-noise operation, and a small value of C can still yield a low corner frequency in the filter.

The rejection of power supply noise is also an important design consideration in such systems. A variety of non-ideal properties of signal processing systems may contribute to signal degradation. In an all-analog signal processor, rectification and distortion can increase in-band noise drastically through mixing of high-frequency power-supply noise. In digital implementations, power-supply noise picked up at the front-end may result in extensive aliasing in the A/D output. Both of these effects indicate the need for broadband power-supply rejection in the front-end system. While in-band power-supply rejection typically is achieved by employing high-gain feedback, as in the sense-amp topology, such feedback only helps when the power-supply noise is modeled as an output disturbance that the feedback attenuates. Indeed, past the closed-loop crossover frequency, $\omega_{CL}$, noise from the supply is contributed with little attenuation. From this perspective it is important to implement filters to limit the total amount of power-supply noise accumulated in the out-of-band region.

In-band power-supply rejection is accomplished with the high-gain feedback that has been discussed above with the sense-amp topology. High frequency supply noise should also be filtered. Several strategies may be employed to achieve this. First, the supply may be filtered directly, loading the entire supply network with passive elements. Most filters of this type may be implemented with inductors. Typically these inductors are prohibitively large for operation at the frequencies of interest and resistive-and-capacitive filters need to be employed. The DC drop produced in resistive-and-capacitive filters may be minimized by using small resistors. Low cutoff frequencies demand a correspondingly larger capacitor making the filter unsuitable for a small-size solution. The Filtering of high-frequency noise at the output of the analog gain stage may also be employed before the A/D conversion. This approach, however, also involves certain shortcomings. Since the output signal of this stage has been given sufficient gain to drive the full-scale input range of the A/D processing system, it is a significant fraction of the supply range. A filter at this stage would require wide-dynamic range to handle the large output signals.

Figure 9:
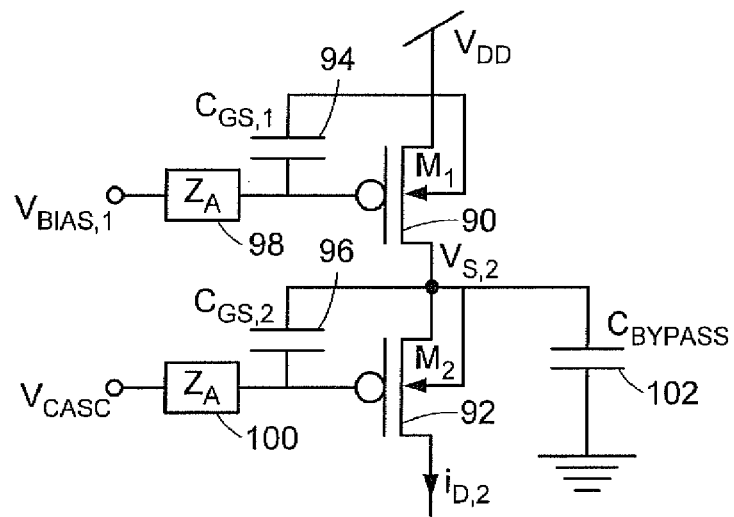
FIG. 9 shows an illustrative diagrammatic schematic view of a power supply decoupling circuit for use in a system in accordance with an embodiment of the invention.
Figure 11:
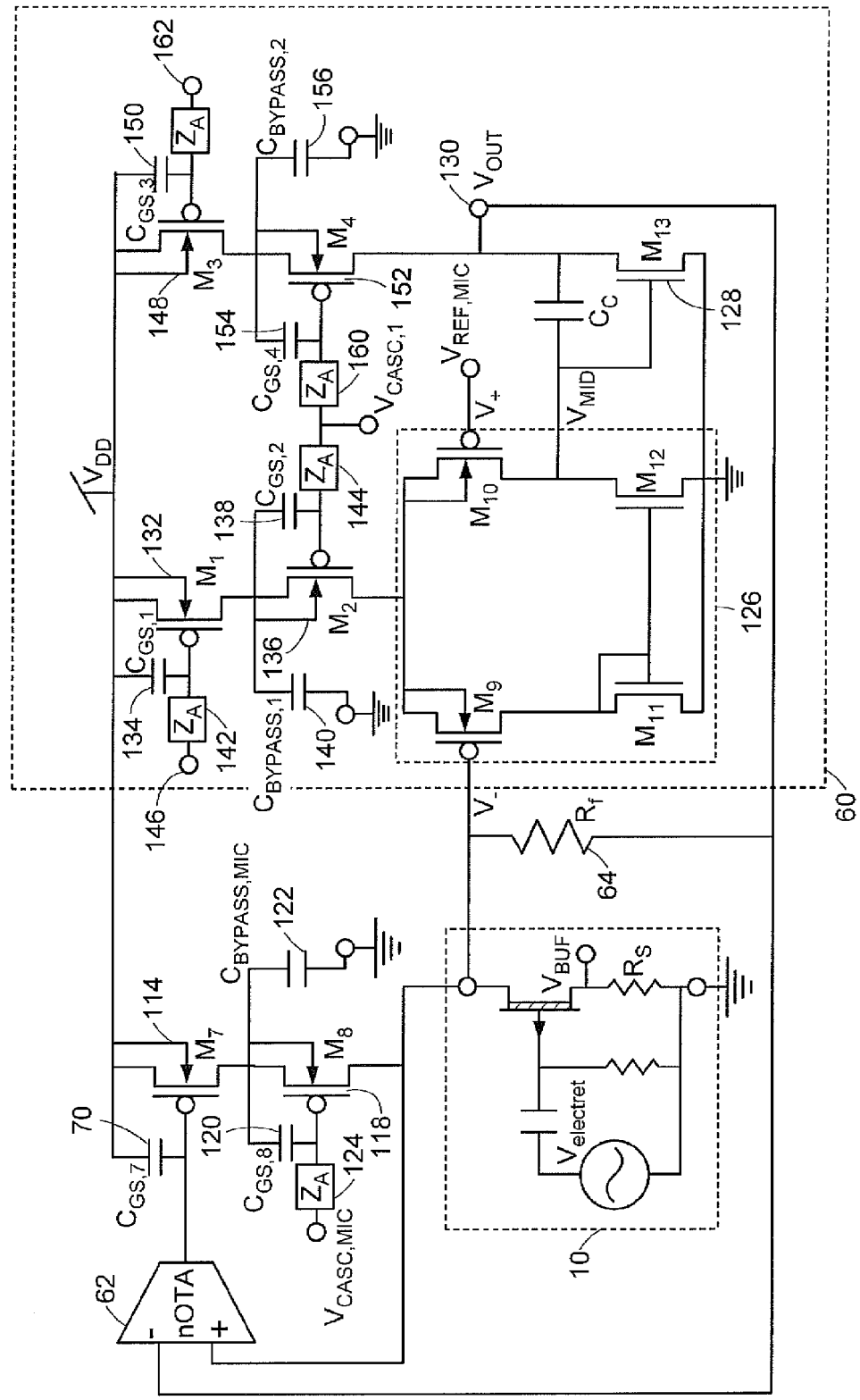
FIG. 11 shows an illustrative diagrammatic view of an amplifier system including a plurality of filter circuits in accordance with another embodiment of the invention.

One approach for power-supply filtering in accordance with an embodiment of the invention is shown in FIG. 9. The system of FIG. 9 shows a supply-bypassing current source that includes two transistors 90, 92 ($M_1$ and $M_2$), a pair of respective gate-source coupled capacitors 94, 96 ($C_{GS,1}$ and $C_{GS,2}$), and two respective impedance networks 98, 100 ($Z_A$ and $Z_B$) as well as a by-pass capacitor 102 ($C_{bypass}$). The bias device, $M_1$, is biased through the large impedance, $z_A$, forming a low-pass filter with the gate-source capacitor, $C_{GS,1}$. The element $z_A$ may be implemented with two parallel diodes with opposite polarity. The strategy yields a DC current source with little response to changes in its source voltage. The gate-source capacitors ($C_{GS,1}$ and $C_{GS,2}$) and the biasing of the p-gates through high impedance elements ($Z_A$ and $Z_B$) make $M_1$ and $M_2$ behave as small-signal large resistances ($g^*_{SD,1}$ and $g^*_{SD,2}$) with the bypass capacitor $C_{bypass}$ filtering the supply voltage before it can affect the bias at $V_{S,2}$ (also $i_{D,1}$). Thus, a current source with supply immunity may be employed in the amplifiers and bias networks in accordance with the present embodiment. Instead of using a single device, a series filter may be provided that shunts high-frequency current away from the other circuits. FIG. 11 shows three such networks employed in an implementation of the amplifier as further discussed below.

Figure 10:
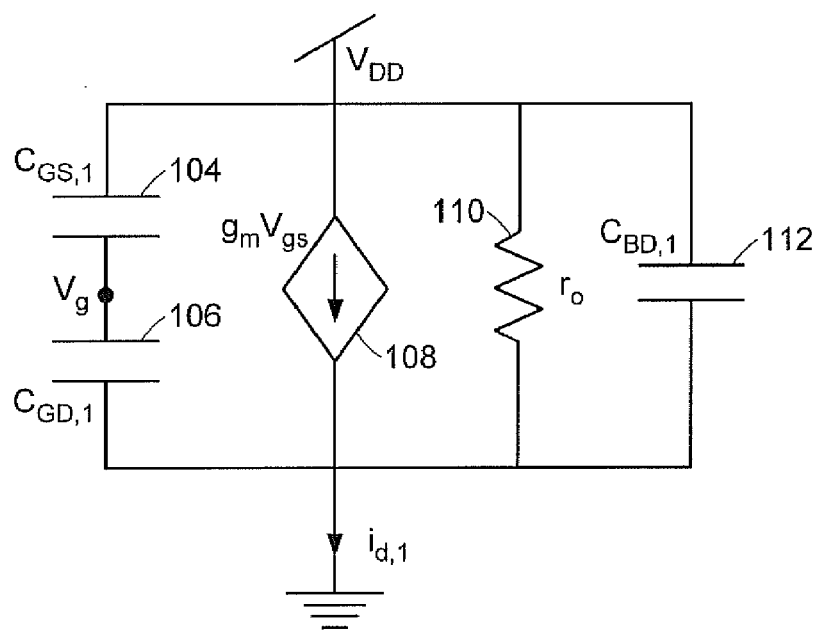
FIG. 10 shows an illustrative diagrammatic view of a small-signal model for one of the devices in the circuit shown in FIG. 9.

The parasitic supply coupling mechanism for a single device arises as follows with reference to the block diagram of FIG. 10, which shows a small signal representation of the bias device, $M_1$ that includes a gate-source capacitive value 104 ($C_{GS,1}$), a gate-drain capacitive value 106 ($C_{GD,1}$), a gain value 108 ($g_m v_{gs}$), a resistive value 110 ($R_o$), and a bulk-to-drain capacitive value 112 ($C_{BD,1}$). Effectively, the whole device may be replaced by a small-signal conductance of value $g_{ds,1}$ given by, $$g_{sd,1} = \frac{i_{d,1}}{v_{dd}} = \left(\frac{C_{GD,1}}{C_{GD,1} + C_{GS,1}}\right) g_{m,1} + \left(\frac{1}{r_o}\right) + s\left(C_{BD,1} + \frac{C_{GD,1} C_{GS,1}}{C_{GD,1} + C_{GS,1}}\right) \quad (8)$$

As $$C_{GS,1} \gg C_{GD,1}, \text{ and } \frac{1}{r_o} \text{ is small,}$$

Equation (8) may be approximated, $$g_{sd,1} \cong \left(\frac{C_{GD,1}}{C_{GD,1} + C_{GS,1}}\right) g_{m,1} + s(C_{BD,1} + C_{GD,1}). \quad (9)$$

The drain capacitances of the bias device, $C_{GD,1}$ and $C_{BD,1}$, limit the isolation of output current, $i_{d,1}$, from variations in the supply voltage, $v_{dd}$. The gate-to-drain capacitance limits the real output impedance of the device by dominating the contribution to $g_{sd,1}$ over the $$\frac{1}{r_o}$$

term in Equation (8) above. Both the gate-to-drain and the bulk-to-drain capacitances contribute to high-frequency feed-through as the last term in Equation (8) and Equation (9) above. Making the gate-to-source capacitance artificially large with an explicit capacitor will help to attenuate the first feed-through term in the right hand side of Equation (9). To provide additional filtering, a second device, $M_2$, in parallel with a filter capacitor, $C_{bypass}$, may be used to obtain low-pass filtering at the intermediate node, $v_{s,2}$. The overall filter characteristic for the output current, $i_{d,2}$, may be approximated from Equation (9) and FIG. 9. Ignoring the large output resistance, r, and the drain capacitances, $C_{BD,1}$ and $C_{GD,1}$, and approximating $g_{sd}$ for $M_1$ and $M_2$ as having purely resistive components, provides:

$$g^*_{sd,1} = \frac{C_{GD,1}}{C_{GD,1} + C_{GS,1}} g_{m,1}, \quad (10)$$

$$g^*_{sd,2} = \frac{C_{GD,2}}{C_{GD,2} + C_{GS,2}} g_{m,2}. \quad (11)$$

The admittance from the supply is $$g_{Supply} = \frac{i_{d,2}}{v_d} = \left(\frac{g^*_{sd,1} g^*_{sd,2}}{g^*_{sd,1} g^*_{sd,2} + sC_{bypass}}\right). \quad (12)$$

The low-pass filtering effect of the bypass capacitor is clear in Equation (12). If the parasitic drain capacitances of both devices are included as, $C_{D,i} = C_{GD,i} + C_{BD,i}$ (assuming $C_{GS} \gg C_{GD}$ in FIG. 10), a limit to the maximum supply rejection is observed from computing the overall supply coupling, $$g_{Supply} = \frac{i_{d,2}}{v_{dd}} = \frac{(g^*_{sd,1} + sC_{D,1})(g^*_{sd,2} + sC_{D,2})}{g^*_{sd,1} + g^*_{sd,2} + s(C_{D,1} + C_{D,2} + C_{bypass})}. \quad (13)$$

Two zeros result from the feed-through caused by the drain capacitances. The pole arises from the high-impedance bypass node produced by both p-devices. By choosing $C_{bypass}$ to be larger than the parasitic drain capacitances, the pole may be made to dominate at lower frequencies, reducing the supply sensitivity at the high-impedance node, $v_{s,2}$ in FIG. 9. At frequencies higher than the corner frequency of this filter, the source voltage at the bypass capacitor has limited attenuation from the supply, $$\frac{v_{s,Min}}{v_{dd}} = \frac{C_{GD,1} + C_{BD,1}}{C_{bypass} + C_{GD,2} + C_{GD,1} + C_{BD,1} + C_{BD,2}} \cong \frac{C_{GD,1} + C_{BD,1}}{C_{bypass}}. \quad (14)$$

Consequently, it is desirable to make the bypass capacitance as large as possible to ensure the best filtering at high-frequencies. The available output range may be reduced, however, due to the presence of a second saturation-region device in the current source of FIG. 9. The supply rejection up to frequencies present in the digital or telemetry system may be achieved, however, if the system supply voltage is not prohibitively low, making this design choice appropriate in certain applications. On a 2.8V power-supply for example, good power-supply rejection may be obtained without losing headroom.

FIG. 11 shows three such cascode filter networks employed in an implementation of the amplifier 60 shown in FIG. 7 together with the self-biased microphone 10, the feedback element 64, and the low frequency feedback amplifier 62. In particular, a microphone bias filter includes transistors 114 ($M_7$) and 118 ($M_8$). The effect of the $V_{DD}$ is substantially eliminated on the output of the transistor 114 ($M_7$) by coupling one of its control terminal to directly to $V_{DD}$ and another to $V_{DD}$ via capacitor 70. One of the control terminals of the transistor 118 ($M_8$) is directly coupled to the microphone output node, while another of its control terminals is coupled to the output of transistor 114 ($M_7$) via a capacitor 120 ($C_{GS,8}$). The output of the transistor 114 ($M_7$) is also coupled to ground via a bypass capacitor 122 ($C_{bypass,MIC}$) to filter the intermediate current before being delivered to the microphone output node. The low frequency control terminal of the transistor 118 ($M_8$) is set through a high impedance element 124 ($Z_A$) to provide noise immunity from the bias voltage $V_{CAS,MIC}$ to provide in effect a low pass filter.

The amplifier 60 includes a first stage amplifier 126 the includes a differential pair with a mirror to produce a single ended output that is biased through an input stage bias filter, and the amplifier 60 includes a second stage amplifier 128 that is biased through an output stage bias filter. The input stage bias filter includes transistors 132 ($M_1$) and 136 ($M_2$). The effect of the $V_{DD}$ on the output of transistor 132 ($M_1$) is substantially eliminated by coupling one of its control terminals to directly to $V_{DD}$ and another to $V_{DD}$ via capacitor 134. One of the control terminals of the transistor 136 ($M_2$) is directly coupled to an input differential pair bias node, while another of its control terminals is coupled to the output of transistor 136 ($M_2$) via a capacitor 138 ($C_{GS,2}$). The output of transistor 132 ($M_1$) is also coupled to ground via a bypass capacitor 140 ($C_{bypass,1}$) to filter the intermediate current before being delivered to the input differential pair bias node. The low frequency control terminals of the transistors 132 ($M_1$) and 136 ($M_2$) are set respectively through high impedance elements ($Z_A$) 142 and 144 respectively to provide noise immunity from the bias voltage $V_{CAS,1}$. The bias current for the input stage is determined by setting the bias input voltage at node 146.

The output stage bias filter includes transistors 148 ($M_3$) and 152 ($M_4$). The effect of the $V_{DD}$ on the output of transistor 148 is substantially eliminated by coupling one of its control terminal directly to $V_{DD}$ and another to $V_{DD}$ via capacitor 150. One of the control terminals of the transistor 152 ($M_4$) is directly coupled to an output node 130, while another of its control terminals is coupled to the output of transistor 152 ($M_4$) via a capacitor 154 ($C_{GS,4}$). The output of $M_3$ is also coupled to ground via a bypass capacitor 156 ($C_{bypass,2}$) to filter the intermediate current before being delivered to the output node. The low frequency control terminals of the transistors 148 ($M_3$) and 152 ($M_4$) are set through high impedance elements ($Z_A$) 158 and 160 respectively to provide noise immunity from the bias voltage $V_{CAS,1}$. The bias current for the output stage is determined by setting the bias output voltage at node 162.

A pre-amplifier and microphone system in accordance with an embodiment may be fabricated using a two-stage topology of the operational amplifier and the overall pre-amplifier circuit. A 2.8V supply may provide power for the circuits and a Knowles Electronics FG-3329 microphone may be used. Resistive feedback and supply decoupling structures in the drain circuits may also be employed. The use of supply filters in all supply biasing may facilitate high-frequency rejection performance. The pMOS input stage may be comprised of differential-pair transistors, current mirror transistors, and supply-decoupling current-source devices. Three such current sources may be used. Transistors may be used to bias the microphone buffer and sense node. The output of a first stage drives another transistor in a second output stage. Bypass capacitors may be shunted to ground, although another quiet reference could be used in other embodiments. The input stage of the operational amplifier may be biased at 6 uA. The input devices may be chosen to obtain a 1/f noise corner near 100 Hz. Compensation of the two-stage amplifier may be achieved with the most robust parasitic conditions in mind—the microphone and auxiliary inputs present capacitive loads to the sense-node, deteriorating the phase margin of the closed loop. Biasing of the second stage may be achieved to ensure load-drive capability for subsequent stages—typically 100 pF. Total power consumption for the two-stage amplifier may be 34 uW. The feedback may be biased with 1-3 nA while the high-frequency feedback element, $R_f$, may be chosen to be approximately 300 k$\Omega$. The microphone operates at approximately 20 uA, adding almost 60 uW to the power consumption. Total power consumption may be measured to be about 94 uW.

Figure 12:
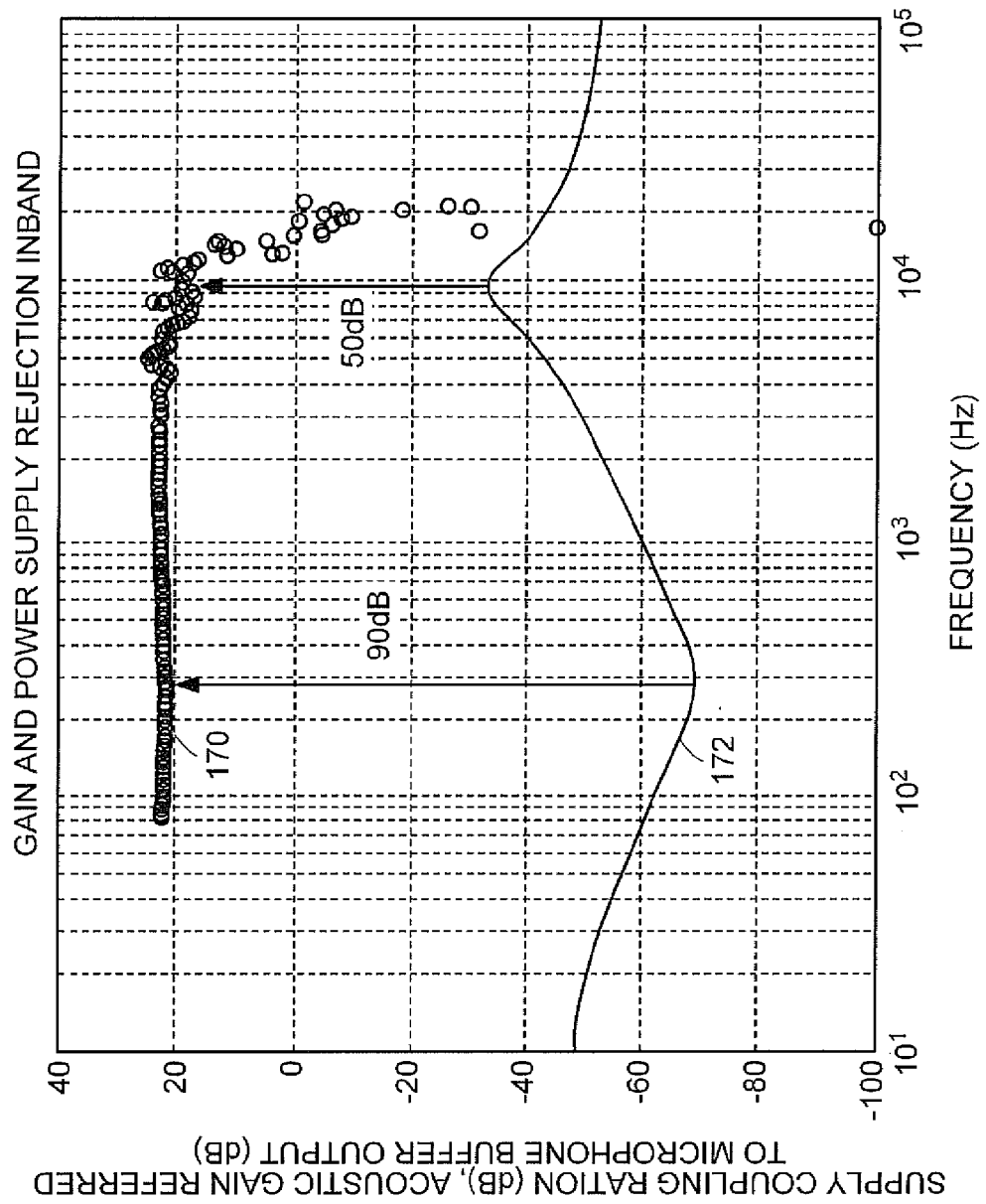
FIG. 12 shows an illustrative diagrammatic graphical representation of a frequency response for gain and power supply rejection in a system in accordance with an embodiment of the invention.

The acoustic gain referenced to the in-band microphone-buffer sensitivity for such a system is shown at 170 in FIG. 12, while the power supply rejection is shown at 172. The FG-3329 has an in-band sensitivity of 17 mV per Pascal at the $v_{buf}$ output in FIG. 2.

Thus, in the curve shown at 170, a gain of 20 dB corresponds to 170 mV/pascal. The measured gain was calibrated with respect to a reference microphone in an anechoic environment. The reference microphone and acoustic environment were calibrated Bruel & Kjaer 4232/4188 systems. At frequencies above 10 kHz, the flatness of the reference microphone degraded. Consequently the gain calibration exhibits peaks and troughs at high-frequencies.

The power supply rejection ratio for the system is the ratio of the voltage gain from $v_{buf}$ to $v_{out}$ with respect to the voltage gain from $v_{dd}$ to $v_{out}$, in FIG. 2. The value $V_{dd}$ is used to power the operational amplifier. The voltage gain from the supply, $v_{dd}$, to the output, $v_{out}$, is the sensitivity of the system to supply variations and is shown at 172 in FIG. 12. The voltage gain from $v_{buf}$ to $v_{out}$ for the in-band audio frequencies is shown at 170 in FIG. 12. Thus, the PSRR in dB may directly be read off as the difference between the top and bottom curves (170, 172) of FIG. 12. At 300 Hz, 90 dB of PSRR is observed, and at 10 kHz, 50 dB of PSRR is observed. Near 10 kHz, the injection of supply noise current excites second-order dynamic behavior in the overall sense-amp producing a peaking effect.

Figure 13:
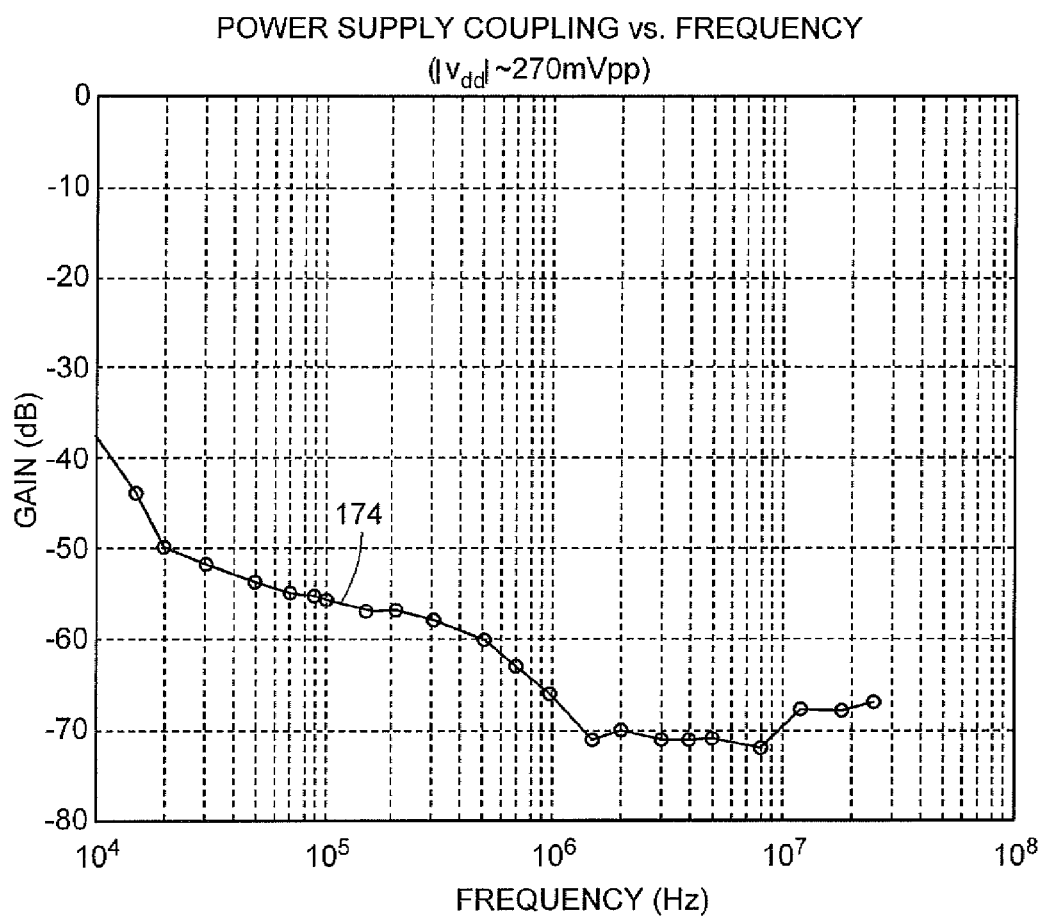
FIG. 13 shows an illustrative diagrammatic graphical representation of power supply coupling versus frequency for a system in accordance with an embodiment of the invention.
Figure 14:
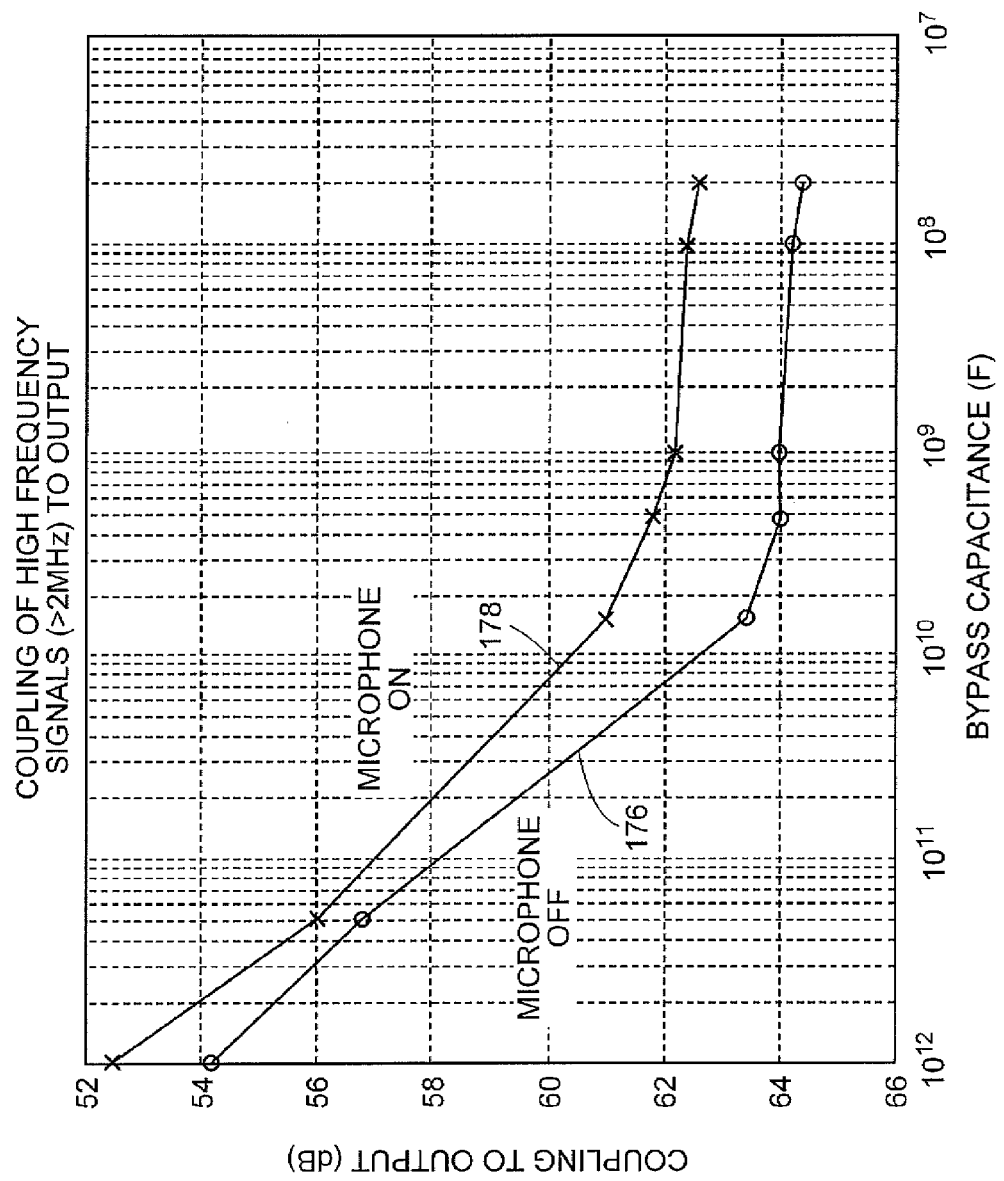
FIG. 14 shows an illustrative diagrammatic graphical representation of the coupling of high frequency signals with the microphone on and off in a system in accordance with an embodiment of the invention.

Measurements were made on the system with all bypass capacitances, $C_{bypass}$, of value 1 nF. To ensure that supply filtering is occurring properly, feed-through data were taken up to 26 MHz. This high-frequency rejection data is shown at 174 in FIG. 13. As expected, feed-through effects flatten-out at frequencies higher than the dynamics of the supply filter indicating that the bypass capacitance is dominating the voltage attenuation at the high-impedance filter nodes. Varying the bypass capacitance, $C_{bypass}$, changes the attenuation ratio directly. As shown in FIG. 14, the high frequency signals are filtered most effectively from the output in the presence of a large bypass capacitor both with the microphone off (as shown at 176) and with the microphone on (as shown at 178). A static protection resistor in the chip's pads limits the attenuation of the decoupling path to −64 dB. Potential clock and telemetry frequencies, such as those greater than 2 MHz, are reasonably attenuated even with small capacitances, e.g., with $C_{bypass}$ of 100 pF. A rough estimate of the parasitic drain capacitance, $C_{GD,1}+C_{BD,1}$, contributing to feed-through is estimated at 28 fF. Beyond bypass capacitances of 500 pF, the coupling to the output does not decrease significantly. This result arises from a static protection resistor built into the chip's pads that limited attenuation.

Figure 15:
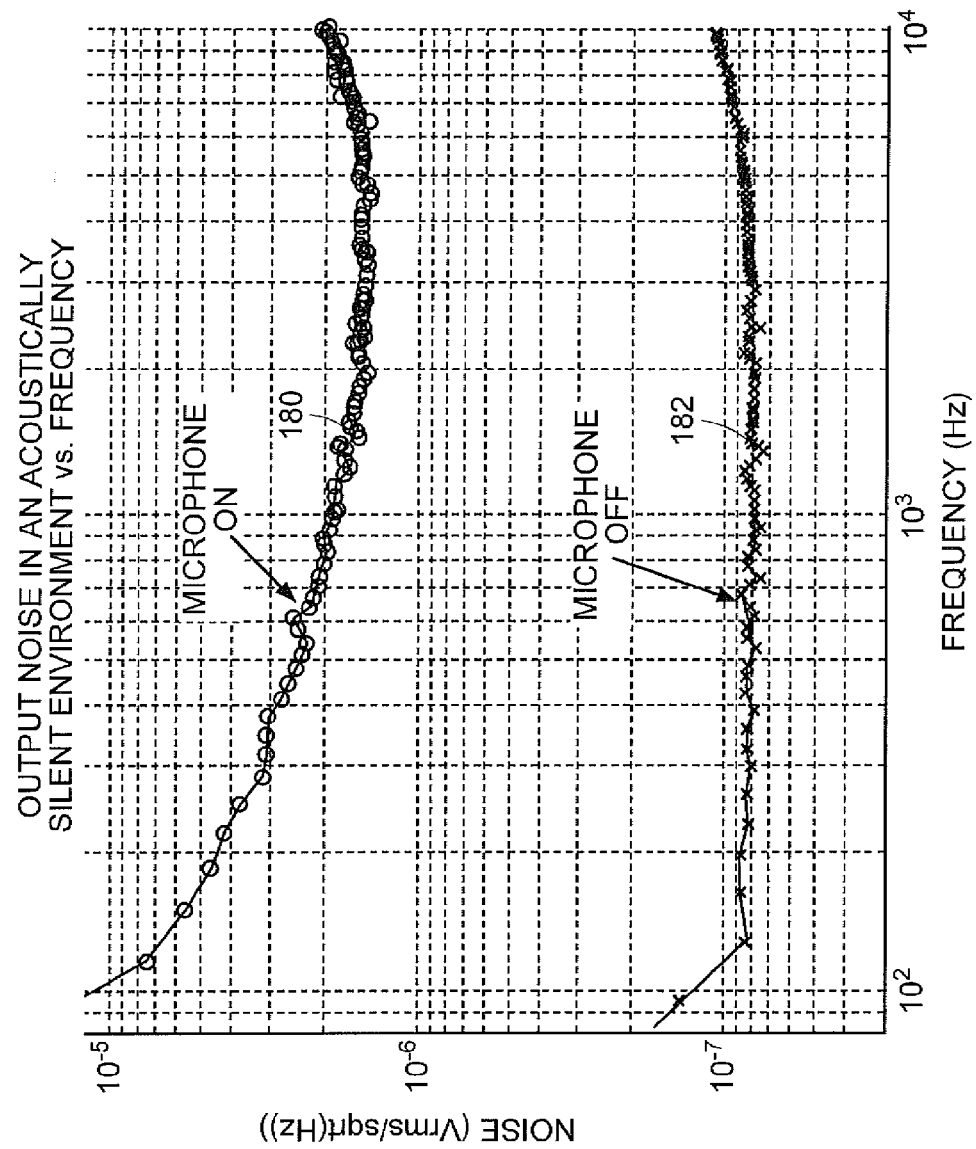
FIG. 15 shows an illustrative diagrammatic graphical representation of output noise versus frequency with the microphone on and off in an acoustically silent environment for a system in accordance with an embodiment of the invention.

The noise performance of the front-end is shown in FIG. 15 with the microphone on (as shown at 180), and with the microphone off (as shown at 182). These relationships confirm that the overall noise performance is not limited by the operational amplifier or low-frequency biasing network but by the microphone. Total output noise is 52 uVrms from 100 Hz to 10 kHz. Referred to the microphone-buffer output/input, this yields an input-referred total noise of 5 uVrms from 100 Hz to 10 kHz.

In further embodiments, an auxiliary voltage-mode input to the sense-amp may be added by sourcing voltage to the sense-node through a resistor, $R_{AUX}$. Noise in the presence of this auxiliary channel was also measured. For a voltage-voltage gain of 20 dB the total output noise is 48 uVrms from 100 Hz to 10 kHz for an $R_{AUX}$ of 30 k$\Omega$ Referred to the microphone-buffer output/input this noise yields an input-referred total noise of 4.8 uVrms from 100 Hz to 10 kHz.

Figure 16:
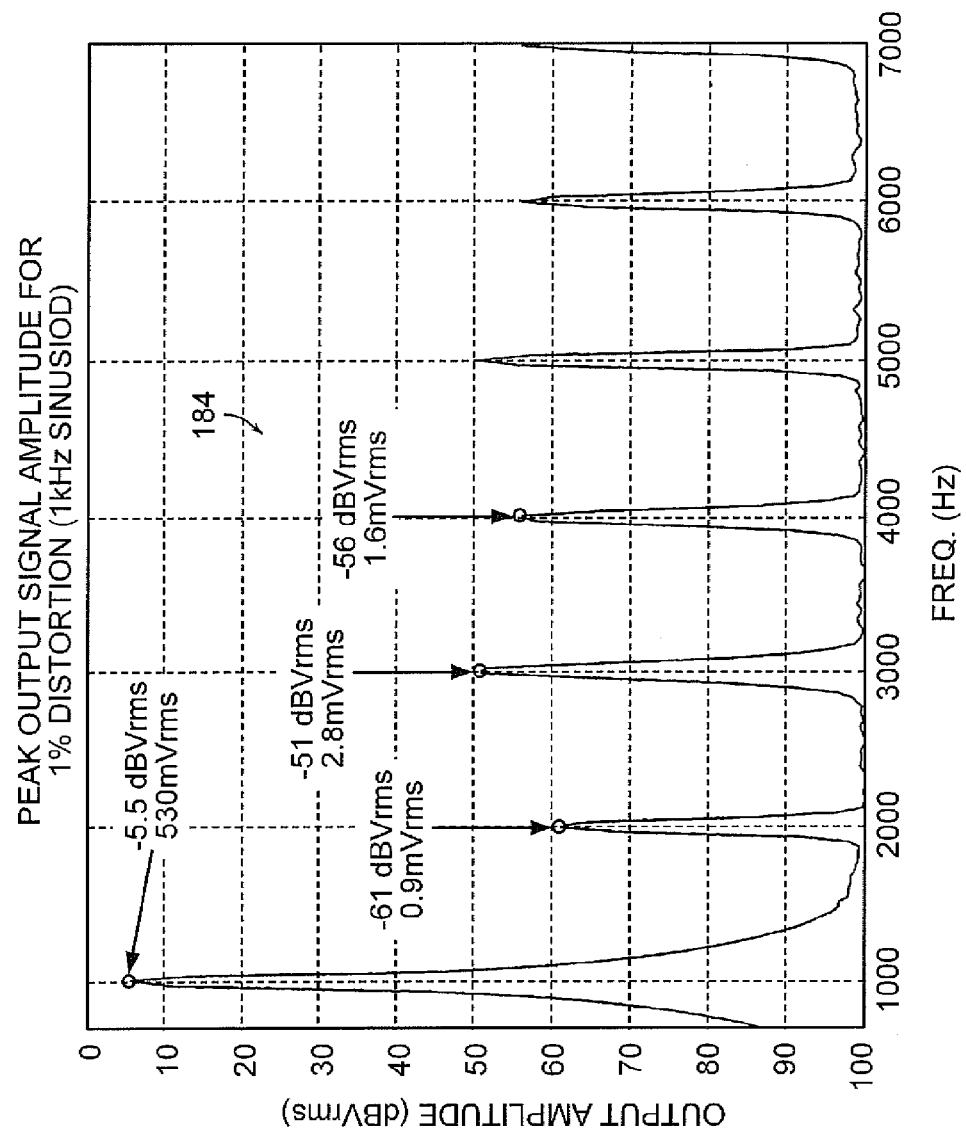
FIG. 16 shows an illustrative diagrammatic graphical representation of peak output signal amplitude for 1% distortion of a 1 kHz sine signal in a system in accordance with an embodiment of the invention.
Figure 17:
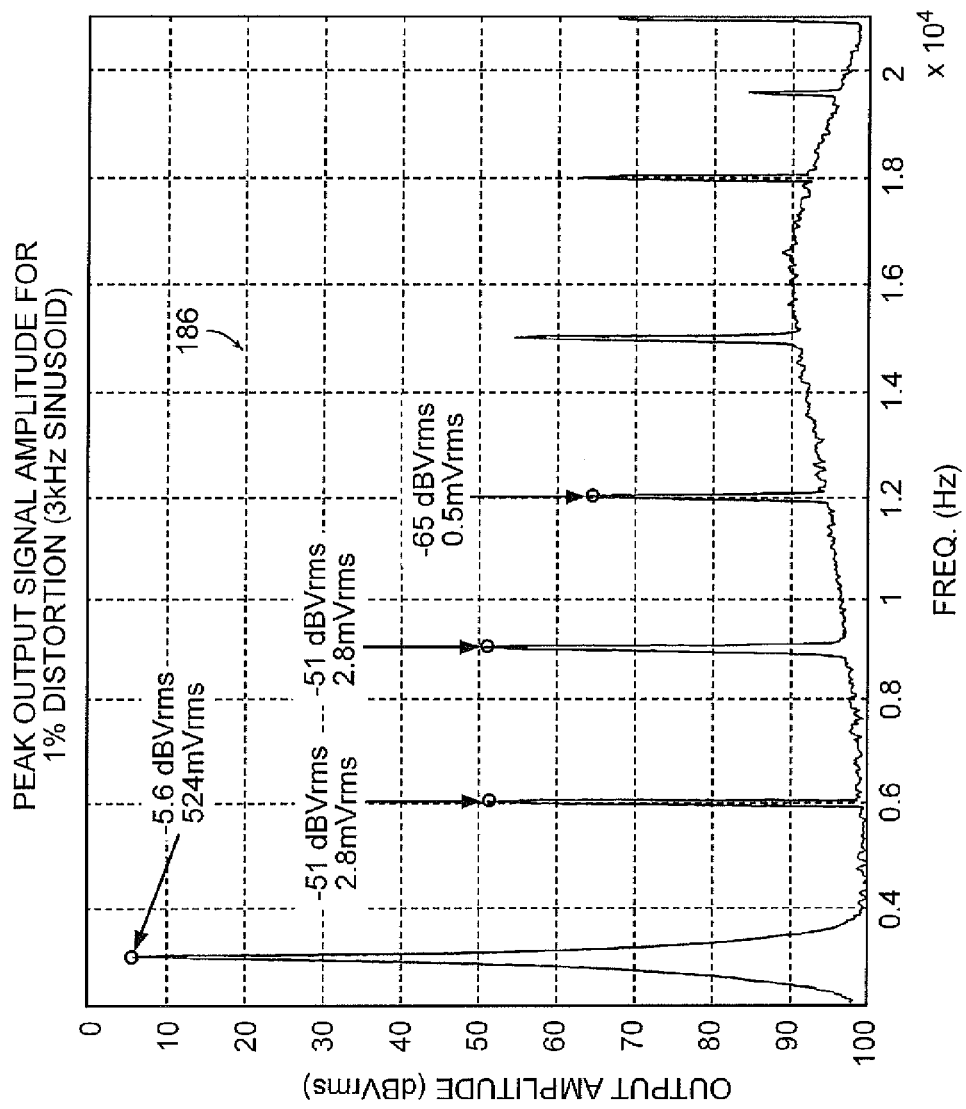
FIG. 17 shows an illustrative diagrammatic graphical representation of peak output signal amplitude for 1% distortion of a 3 kHz sine signal in a system in accordance with an embodiment of the invention.

It has also been found that the output voltage linear range was limited somewhat by the power-supply rejection networks. A total harmonic distortion metric of 1% was chosen for best audio performance. A maximum output signal amplitude of 530 mVrms was obtained for 100 Hz to 3 kHz operation with-less than 1% distortion. Above 3 kHz, second order distortion due to feed-through in the low-frequency bias loop was observed. In FIGS. 16 and 17, the transition between the well-behaved distortion characteristics and high-frequency effects are shown at 184 and 186 respectively.

Figure 18:
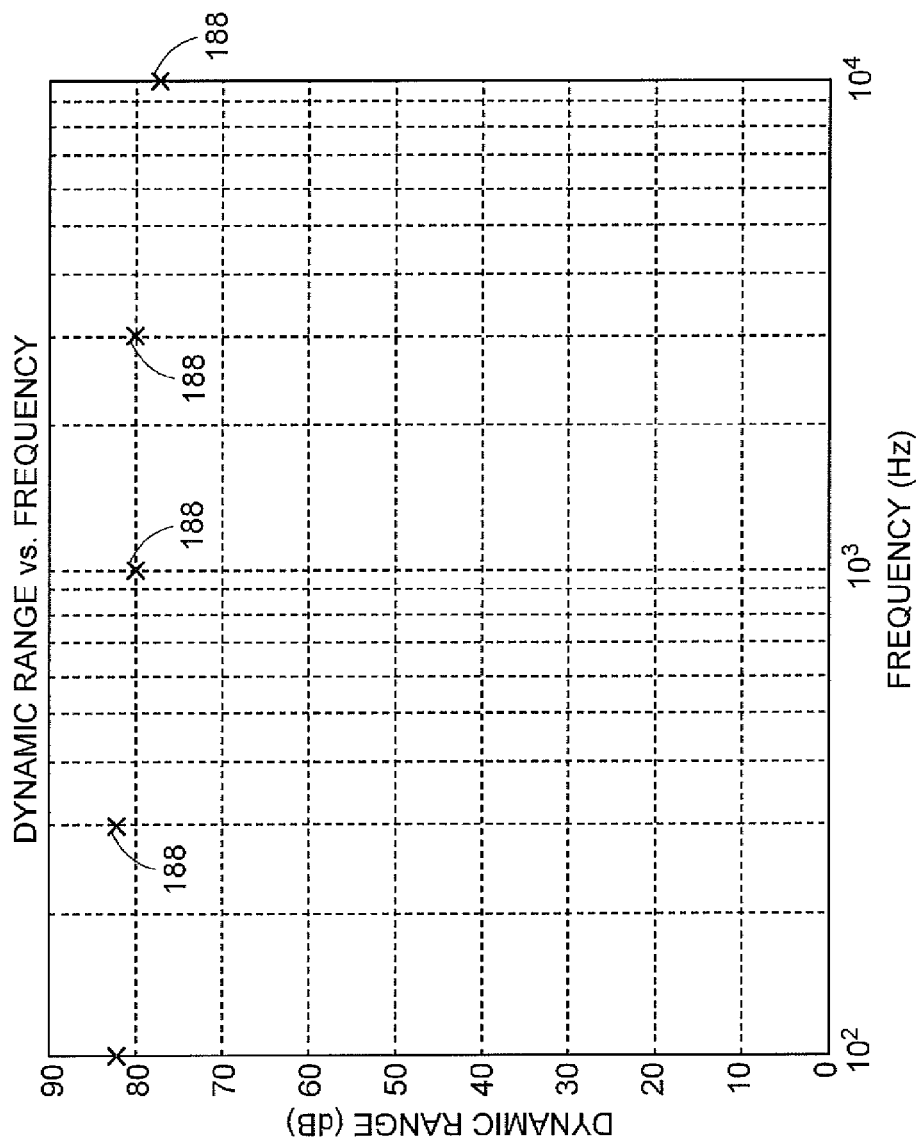
FIG. 18 shows an illustrative diagrammatic graphical representation of the relationship between dynamic range and frequency for various frequencies in a system in accordance with an embodiment of the invention.

FIG. 18 shows at 188 the dynamic range as a function of frequency for the microphone transduction system for 1% distortion limits and a minimum detectable signal of 5 µVrms as a function of frequency. The dynamic range varies from 82 dB to 78 dB from 100 Hz to 10 kHz. Both linear range and noise performance are summarized in Tables 1 and 2 below respectively.

TABLE 1

| Condition | Total Output Noise (100 Hz-10 kHz) (Vrms) | Total Input Noise (100 Hz-10 kHz) (Vrms) | Maximum Output Range for 1% Distortion (Vrms) | Maximum Input Range for 1% Distortion (Vrms) |
|---|---|---|---|---|
| Microphone at 20 dB gain Auxiliary Off | 52 μVrms | 5 μVrms | 530 mVrms | 52 mVrms |
| Microphone off Auxiliary at 20 dB gain | 48 μVrms | 4.8 μVrms | 510 mVrms | 51 mVrms |
| Microphone and Auxiliary at 20 dB gain | ~100 μVrms | ~10 μVrms | 510 mVrms | 51 mVrms |

TABLE 2

| Specification | Measured |
|---|---|
| Power Consumption | 96 μW |
| Dynamic Range at 1% distortion | 80 dB |
| Minimum Detectable Signal | 5.2 μVrms (microphone on) 4.8 μVrms (auxiliary on) |
| PSRR in-band | >50 dB-90 dB |
| Gain Flatness (auxiliary input) | 1 dB |

Cochlear implants with telemetry and mixed-signal processing require versatile, low-power, and broadband supply-resilient transduction for input signals. The 94 μW, 80 dB current-mode sense-amplifier topology discussed above in accordance with an embodiment addresses these needs by implementing pre-emphasis filtering, DC-biasing control, and achieving an in-band supply rejection of 50-90 dB. A simple power-supply filtering network makes broad-band supply-independent operation possible well into the tens of MHz range. Systems of the invention are useful for preamplifying sound from buffered electret microphones that are widely used in hearing aids and cochlear implants.

Those skilled in the art will appreciate that numerous modifications and variations may be made to the above disclosed embodiments without departing from the spirit and scope of the invention.

What is claimed is:

1. A low power high dynamic range microphone amplification system comprising a current sensing amplifier for receiving an input current signal representative of auditory information and for providing an amplifier output signal, said current sensing amplifier including a DC bias network that includes a cascode filter for removing low frequency current and DC current before being delivered to a sensing node using a feedback arrangement having a high frequency feedback path including a low frequency filter, and a low frequency feedback path including a high frequency filter.

2. The system as claimed in 1, wherein the cascode filter includes a first capacitor that is coupled between two terminals of a first transistor.

3. The system as claimed in 2, wherein the cascode filter includes a second capacitor that is coupled between two terminals of a second transistor.

4. The system as claimed in 1, wherein the cascode filter includes a first transistor is configured to provide a current source, and a second transistor that acts as a high-impedance element for high-frequency currents.

5. The system as claimed in 1, wherein the cascode filter includes a first transistor and a second transistor, wherein a first current terminal of the first transistor is coupled to a constant voltage, a control terminal of the first transistor is coupled to a high-impedance element, and a second current terminal of the first transistor is coupled to a first current terminal of a second transistor.

6. The system as claimed in claim 5, wherein a control terminal of the second transistor is coupled to a high-impedance element, and a second current terminal of the second transistor is coupled to at least one bias node in the current sensing amplifier.

7. The system as claimed in claim 1, wherein the cascode filter is coupled to a microphone output node.

8. A low power high dynamic range microphone amplification system comprising:
   a self-biased microphone circuit that provides a current signal that is representative of auditory information;
   a current sensing amplifier for receiving the current signal at an amplifier input node and providing an amplifier output signal at an amplifier output node; and
   a feedback network including a high frequency feedback path including a low frequency filter, and a low frequency feedback path including a high frequency filter, said feedback network is configured to remove undesirable low frequency current and DC current.

9. The system as claimed in claim 8, wherein said low frequency feedback path includes an amplifier, a low pass filter and a current source.

10. The system as claimed in claim 9, wherein said amplifier is a wide linear range transconducting amplifier.

11. The system as claimed in claim 8, wherein said current source includes a cascode filter.

12. The system as claimed in claim 10, wherein the current source includes a bypass capacitor.

13. A transistor current source comprising a first transistor including a supply voltage node, a control signal node and an output current node, and a second transistor including a current receiving node for receiving current from the first transistor, a control node and an output node, wherein the output node of the first transistor is coupled to the current receiving node of the second transistor and is coupled to a first filter element for providing a DC current source having minimal response to changes in a source voltage node using a feedback network including a high frequency feedback path including a low frequency filter, and a low frequency feedback path including a high frequency filter.

14. The system as claimed in claim 13, wherein the first filter element is a capacitor.

15. The system as claimed in claim 13, wherein the control terminal of the first transistor is coupled to the supply voltage node of the first transistor by a second filter element.

16. The system as claimed in claim 15, wherein the control terminal of the second transistor is coupled to the current receiving node of the second transistor by a third filter element.

17. The system as claimed in claim 16, wherein the second and third filter elements are capacitors.

18. The system as claimed in claim 16, wherein the control terminal of the first transistor is coupled to a first bias voltage and the control terminal of the second transistor is coupled to a second bias voltage.

19. The system as claimed in claim 18, wherein the control terminal of the second transistor is coupled to the second bias voltage via a high impedance element.

* * * * *